US005522817A

United States Patent [19]
Sander et al.

[11] Patent Number: 5,522,817
[45] Date of Patent: Jun. 4, 1996

[54] ABSORBABLE SURGICAL FASTENER WITH BONE PENETRATING ELEMENTS

[75] Inventors: Thomas W. Sander, Newtown; Jeffrey S. White, Ridgefield, both of Conn.

[73] Assignee: United States Surgical Corporation, Norwalk, Conn.

[21] Appl. No.: 201,049

[22] Filed: Feb. 24, 1994

Related U.S. Application Data

[63] Continuation of Ser. No. 875,523, Apr. 27, 1992, abandoned, which is a continuation of Ser. No. 566,242, Aug. 13, 1990, abandoned, which is a continuation-in-part of Ser. No. 332,355, Mar. 31, 1989, abandoned.

[51] Int. Cl.⁶ .............................. A61B 17/56; A61B 17/00
[52] U.S. Cl. ................... 606/72; 606/77; 606/79
[58] Field of Search .......................... 606/72–79, 80, 606/61–68, 219, 220; 623/16, 17, 20

[56] References Cited

U.S. PATENT DOCUMENTS

| | | |
|---|---|---|
| 2,121,193 | 6/1938 | Hanicke . |
| 2,302,559 | 7/1940 | La Place . |
| 2,532,296 | 12/1950 | Giesen . |
| 2,772,676 | 12/1956 | Pohl . |
| 3,209,754 | 8/1961 | Brown . |
| 3,494,243 | 2/1970 | Kleinhenn . |
| 3,605,123 | 9/1971 | Hahn . |
| 3,623,164 | 11/1971 | Bokros . |
| 3,739,773 | 6/1973 | Schmitt et al. . |
| 3,877,080 | 4/1975 | Olcott . |
| 3,915,162 | 10/1975 | Miller . |
| 3,971,134 | 7/1976 | Bokros . |
| 3,986,212 | 10/1976 | Sauer . |
| 4,052,988 | 10/1977 | Doddi et al. . |
| 4,060,089 | 11/1977 | Noiles .......................... 602/220 |
| 4,145,764 | 3/1979 | Suzuki et al. . |
| 4,164,794 | 8/1979 | Spector et al. . |
| 4,263,903 | 4/1981 | Griggs ........................... 606/75 |
| 4,278,091 | 7/1981 | Borzone ......................... 606/75 |

(List continued on next page.)

FOREIGN PATENT DOCUMENTS

| | | |
|---|---|---|
| 127994 | 12/1984 | European Pat. Off. . |
| 273872 | 7/1988 | European Pat. Off. . |
| 283217 | 9/1988 | European Pat. Off. . |
| 346033 | 12/1989 | European Pat. Off. . |
| 2721075 | 11/1978 | Germany . |
| 272107 | 11/1978 | Germany . |
| WO/8701595 | 3/1987 | WIPO . |

OTHER PUBLICATIONS

"Orthosorb Absorbable Pin", brochure by Johnson & Johnson orthopaedics.
"Biofix C" Brochure.
"Richards Fixation Staples", Catalogue of Richards Medical Co.
"Kirschner Wires", Catalogue of Richards Medical Co.
"LCR System Application" Brochure of Instrument Maker Co.
The Journal of Bone and Joint Surgery, "Treatment of Ununited Fractures of the Scaphoid by Iliac Bone Grafts and Kirschner–Wire Fixation," by Herbert H. Start, M.D. et al.
Clinical Materials, "Healing of epiphvseal fracture fixed with a biodegradable polydioxanone implant or metallic pins".
Journal of Bone and Joint Surgery, "Biodegradable Internal Fixation for Malleolar Fractures" by Bostman et al.
Journal of Hand Surgery "Arthrodesis of small joints of the hand: A rapid and effective technique", by J. T. McGlynn, M.D. et al.
European Patent Search Report, Application No. 90303523.6.
European Patent Search Report, Application No. 91713567.1.

*Primary Examiner*—Michael A. Brown

[57] ABSTRACT

A self-inserting absorbable orthopedic fixation device having a bioabsorbable fastening body portion for fastening body tissue, and having bone penetrating elements such as hard, pointed tips for penetrating bone or hard tissue fixed thereto. The pointed tips may be fabricated from metals or ceramics. The fixation device may be in the form of staples, pins, screws, and the like.

38 Claims, 7 Drawing Sheets

U.S. PATENT DOCUMENTS

| | | | |
|---|---|---|---|
| 4,414,966 | 11/1983 | Stednitz. | |
| 4,428,376 | 1/1984 | Mericle. | |
| 4,454,875 | 6/1984 | Pratt | 606/75 |
| 4,463,753 | 8/1984 | Gustilo. | |
| 4,539,981 | 9/1985 | Tunc | 606/77 |
| 4,570,623 | 2/1986 | Ellison | 606/75 |
| 4,592,346 | 6/1986 | Jurgutis. | |
| 4,599,085 | 7/1986 | Riess et al.. | |
| 4,612,923 | 9/1986 | Kronenthal | 606/75 |
| 4,628,923 | 12/1986 | Medoff. | |
| 4,655,222 | 4/1987 | Florez | 606/75 |
| 4,671,280 | 6/1987 | Dorband | 606/220 |
| 4,711,232 | 12/1987 | Fischer et al.. | |
| 4,719,917 | 1/1988 | Barrows | 606/220 |
| 4,756,307 | 7/1988 | Crowninshield. | |
| 4,838,264 | 6/1989 | Bremer | 606/72 |
| 4,858,603 | 8/1989 | Clemow | 606/77 |
| 4,863,444 | 9/1989 | Blömer. | |
| 4,944,742 | 7/1990 | Clemow et al.. | |

ABSORBABLE SURGICAL FASTENER WITH BONE PENETRATING ELEMENTS

CROSS REFERENCE TO RELATED APPLICATIONS

This is a continuation of application Ser. No. 07/875,523 filed on Apr. 27, 1992 which is a continuation of Ser. No. 07/566,242 filed Aug. 13, 1990 which is a continuation-in-part of Ser. No. 07/332,355 filed Mar. 31, 1989 all abandoned.

BACKGROUND OF THE INVENTION

1. Field of the Invention

This invention relates to surgical fasteners for fastening body tissue and more particularly relates to an at least partially absorbable fastener for fastening bone or hard tissue.

2. Background of the Related Art

Bone fastening or fixation devices are well known in the art. Typically, such fasteners are in the form of staples, pins, screws, and wires. For example, both Pratt et al., U.S. Pat. No. 4,454,875 and Ellison et al., U.S. Pat. No. 4,570,623 disclose staples for being driven into bones. Staples of this type are generally fabricated of biologically inert metal, such as stainless steel, titanium, cobalt-chromium-molybdenum alloys and the like. The staple must be relatively strong and hard so that it can be easily driven directly into bone or hard tissue.

Other metal fasteners are well known commercial products used for a wide variety of bone fixation procedures. Pins and wires are generally constructed from stainless steel and are grasped in a drill chuck and self-drilled directly into bone to treat a given traumatic or pathological condition.

The disadvantage of metal fasteners is that after they have completed their function of supporting the bone while the bone heals, they remain permanently in the body. Problems can arise after healing, for example, by corrosion of the metal, or when the pins or staples work loose from their moorings and migrate through body tissue.

Furthermore, permanent metal fixation devices shield the bone from beneficial stresses after healing. It has been shown that moderate periodic stress on bone tissue, such as the stress produced by exercise, helps to prevent decalcification of the bone. Under some conditions, the stress shielding which results from the long term use of metal bone fixation devices can lead to osteoporosis.

These disadvantages can be mitigated by the use of bioabsorbable surgical fasteners, which degrade over a period of time thereby gradually transferring more support load to the bone as it heals. Such fasteners for bone are also known in the art. For instance, Tunc, U.S. Pat. No. 4,539,981 teaches the use of polymers of L(–)lactide for fabricating bone fixation devices. Moreover, various types of bioabsorbable pin fasteners have been commercialized. For example, some types of pins are fabricated from poly (p-dioxanone) and are indicated for use to fix in place small bony fragments in the knee and hand, where such fragments are not in tension. As is characteristic for all such absorbable pins, holes must be previously drilled into the bone in order for the pins to be inserted. Bioabsorbable fasteners are not self-inserting, i.e. they are not capable of being driven or screwed directly into bone because the polymeric material they are made of is relatively soft. The necessity to predrill holes in the injured bone adds to the surgical procedures and lengthens the time required to complete the operation.

Up to now, there has been no surgical bone fastener which retained the advantages of the above mentioned types of fasteners, without the concurrent disadvantages.

SUMMARY OF THE INVENTION

Accordingly, it is one object of the present invention to provide a surgical fastener for bone or hard tissue.

It is another object of the present invention to provide a fastener which can be implanted directly into bone or hard tissue.

It is yet another object of the present invention to provide a surgical fastener which is at least partially bioabsorbable.

These and further objects are achieved herein by providing a self-inserting surgical fastener, said surgical fastener comprising a bioabsorbable fastening body portion having at least one bone penetrating element, and further by implanting said surgical fastener into segments of bone or hard tissue, said bioabsorbable fastening body portion maintaining said segments in close adjacency for a period of time sufficient to promote healing. The bone penetrating element of the surgical fastener is of sufficient length to be gripped by a drilling means and inserted into bone or hard tissue. The bioabsorbable fastening body portion is preferably uniform in cross-section, i.e., it is not tapered.

DETAILED DESCRIPTION OF THE INVENTION

The basis of the present invention is the attachment of bone penetrating elements to bioabsorbable polymer implant devices, such as fasteners, thereby enabling the implant devices to be drilled or driven directly into bone or other hard tissue. Common types of bone fasteners include staples and pins, illustrated in the inventive embodiments by FIGS. 1 and 2, respectively.

The fastening body portion of the bone fixation device of the present invention is fabricated from a biodegradable material such as one or more of the several types of bioabsorbable polymers commonly used in such applications. Examples include poly (p-dioxanone), polylactide, polyglycolides, polycaprolactone, poly (orthoesters) and trimethylene carbonate polymer and the like, as well as copolymers and/or mixtures and blends of the same. Optionally, the biodegradable material used in the various embodiments of this invention, may contain reinforcing fibers, so as to produce a high strength composite. The reinforcing fibers can be, for example, polymeric, or ceramic materials, and either bioabsorbable or permanent.

The terms "biodegradable" and "bioabsorbable" are used interchangeably herein, and refer to materials which are chemically broken down and/or assimilated by human (or animal) body tissue.

The bone penetrating elements of the fastener of the present invention are preferably in the form of relatively hard tips for initially contacting the bone and enabling the fastener to penetrate the bone when a suitable driving force is applied. The tips preferably have means for cutting bone or hard tissue such as a relatively sharp point or one or more sharp edges.

The tips should be of sufficient size and mass relative to the fastening body portion of the surgical fastener, to have the mechanical strength necessary to penetrate bone or hard tissue. However, because the material best suited for fabricating the tips is non-biodegradable, the optimum size of the tips is the minimum size necessary to perform its function of penetrating hard tissue and bone for those surgical applications in which the tips will remain embedded in the bone. As discussed below, not all surgical applications require the bone penetrating tips to remain embedded in bone.

FIGS. 1A, 1B, 1C and 1D illustrate a staple type fastener 100 of the present invention, which comprises a fastening body portion 101 for fastening body tissue. The fastening body portion 101 is optimally an integral single piece construction having a crosspiece 103 and legs 102. Legs 102 extend substantially perpendicularly from the crosspiece 103.

Figure 1A:
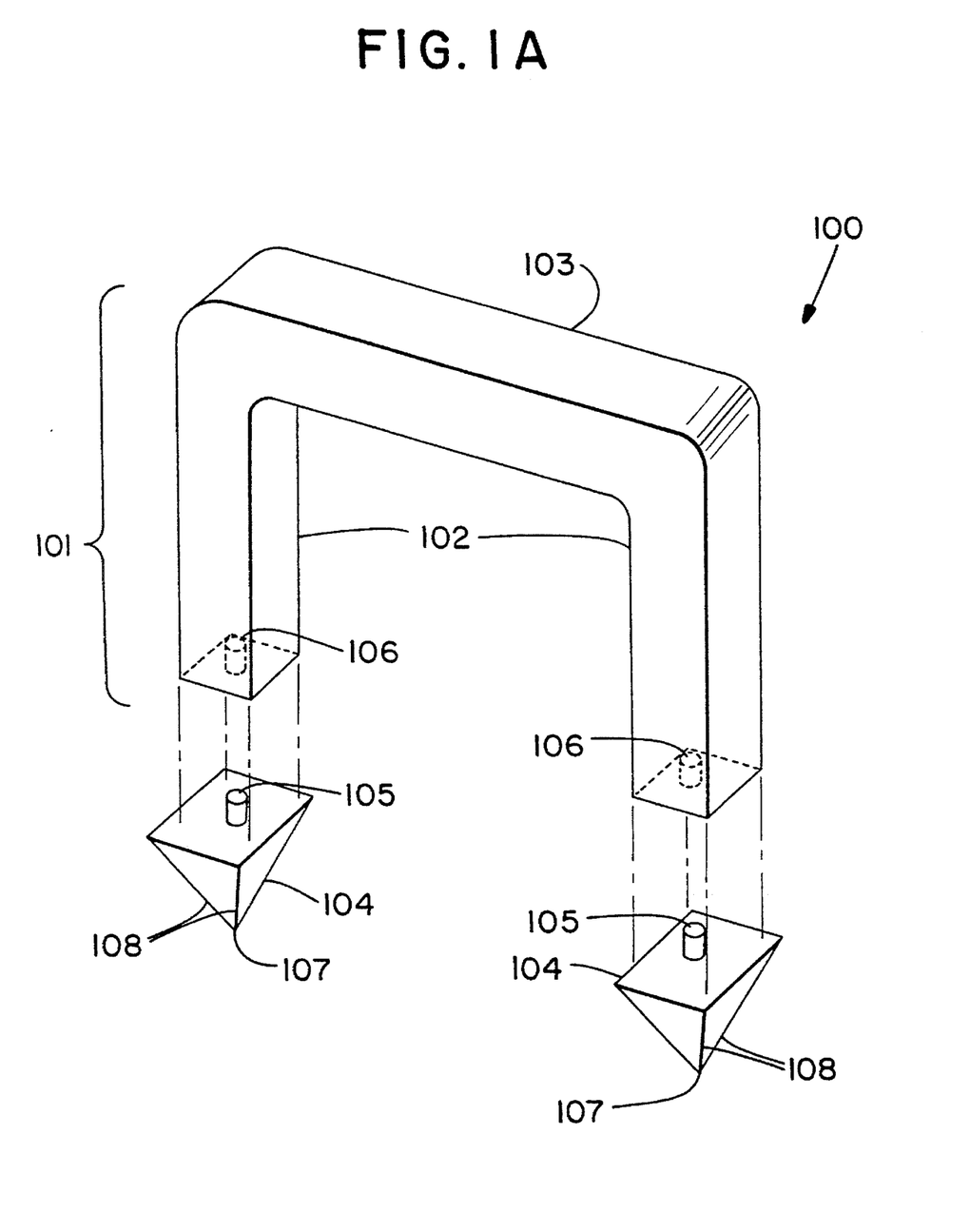
FIG. 1A illustrates an exploded perspective view of the staple type bone fastener of the present invention.
Figures 1B, 1C:
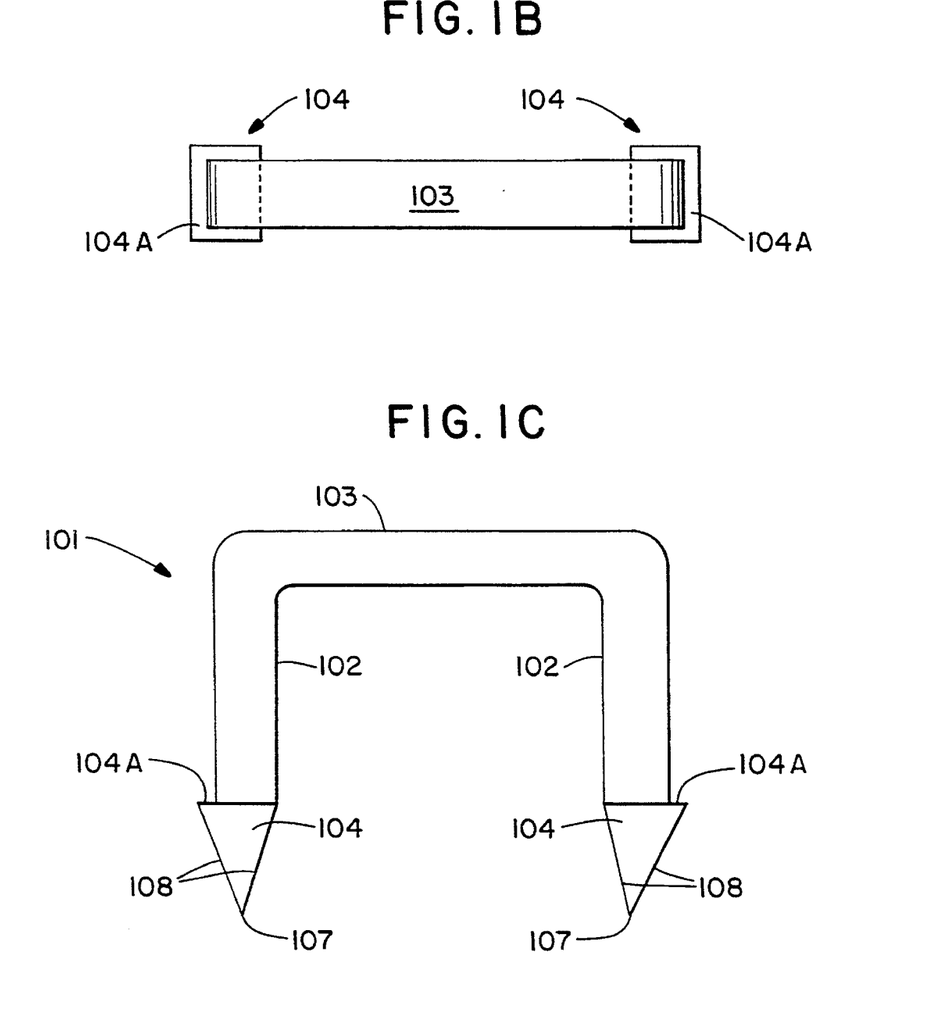
FIGS. 1B, 1C and 1D illustrate, respectively, top, side, and bottom views of the staple type bone fastener of the present invention.
Figure 1D:
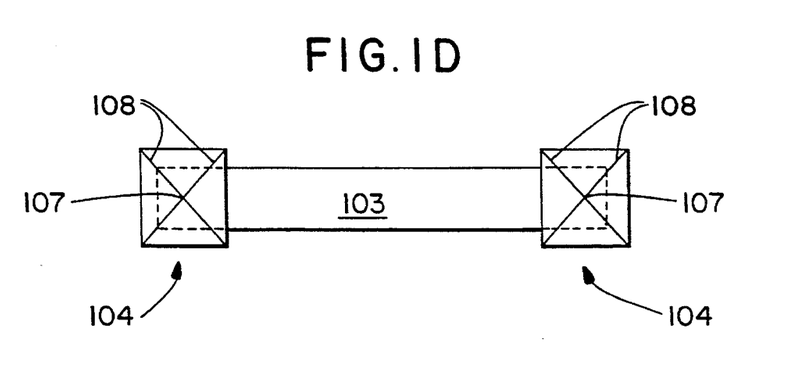

The fastening body portion 101 as shown in FIGS. 1A and 1C is U-shaped, with legs 102 extending from the ends of the crosspiece 103. Alternatively, the legs 102 may be spaced inward from the ends of crosspiece 103, the invention can have one or more legs, and although the legs 102 are illustrated as being of substantially equal length, legs of unequal length are also contemplated as being within the scope of this invention. The legs are substantially uniform in cross-section.

Unlike prior art fasteners, the fastening body portion 101 of the present surgical fastener 100 has one or more bone penetrating elements such as tips 104 attached to the distal ends of legs 102, for penetrating bone or hard tissue. The tips 104 must have a hardness sufficient for such penetration. Thus, tips 104 are preferably made of a metal, such as stainless steel, titanium and its alloys, cobalt-chromium-molybdenum alloys, or other implant grade metal alloys. Ceramics having appropriate hardness and toughness may also be used, such as zirconia, aluminum oxide, carbon/carbon composites, etc. The tips 104 each have a relatively sharp point 107 for easier bone penetration, but any appropriate shape which will perform the same penetrating function may be employed. Also the tips 104 may have backward pointing barbs (not shown) to prevent removal of the fastener.

Each tip 104 has a rearward projecting bolt 105 which engages and is received in a corresponding cavity 106 in the distal end of the respective leg 102. The tips 104 can be attached to the distal ends of the legs 102 by various alternative means. For example, the bolts 105 may be threaded, and cavity 106 may be tapped to form a screw fit. The joint is preferably secured by mounting the tips 104 additionally with a biocompatible adhesive. Or the tips 104 may be fused to the legs 102 by ultrasonic welding, or induction heating.

Referring to FIGS. 1B and 1C, tips 104 have an impact surface 104A for receiving a driving force for implanting the fastener. The impact surface 104A is perpendicular to the direction of the driving force and extends outwardly beyond the surface of the legs 102 on three or fewer sides of each leg. The impact surface does not extend beyond the interior surfaces of the leg 102 into the space between the two legs. As can be seen from FIGS. 1B, 1C and 1D, the edges of the tips 104 are flush with the inside surfaces of the legs 102, thereby preserving a tight fit with minimal latitude for loose movement or play in the fastener once implanted.

Tips 104 optionally have sharp points 107 and edges 108 for cutting through bone and hard tissue, so as to facilitate implantation of the fastener 100.

Figure 1E:
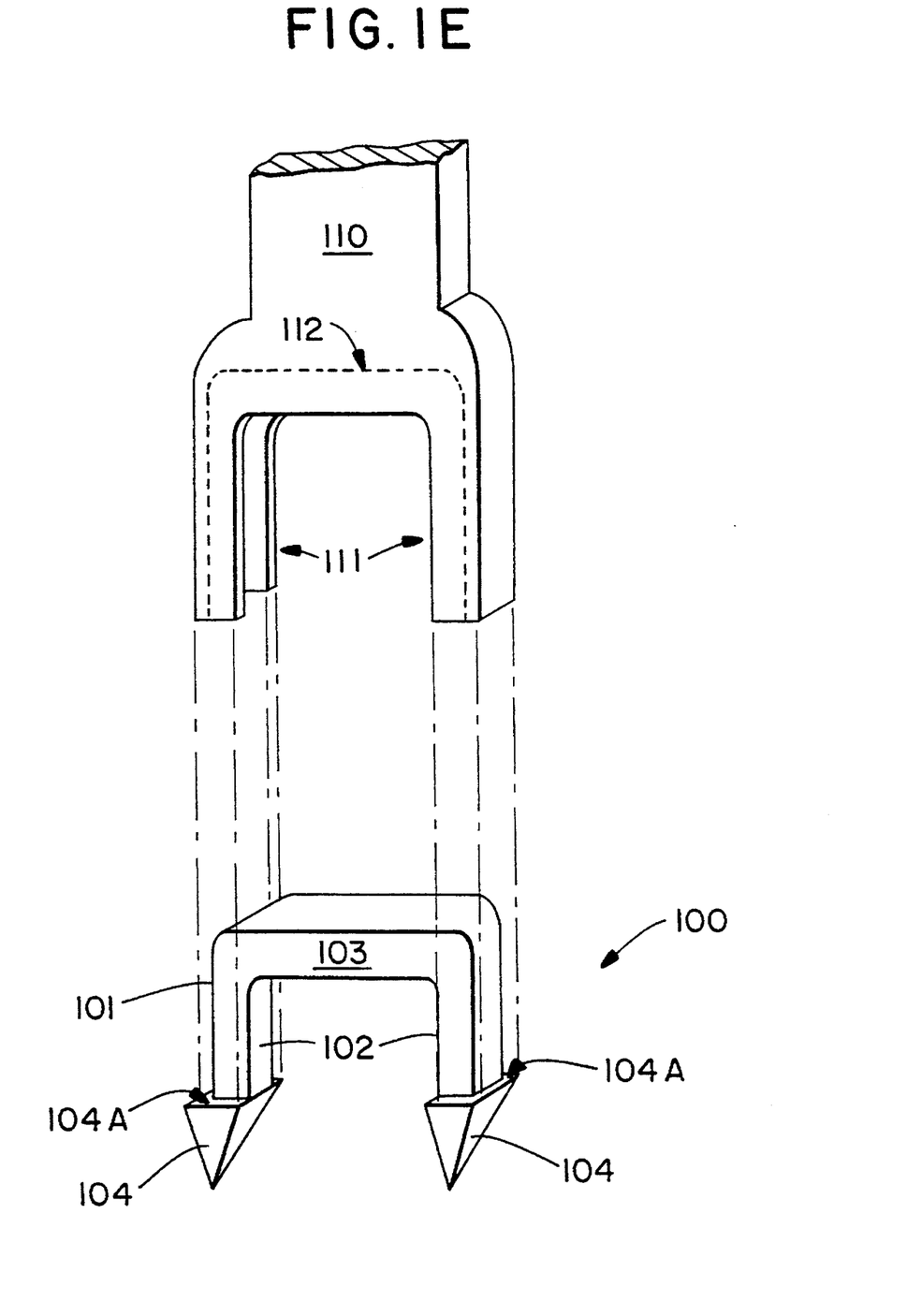
FIG. 1E illustrates the staple type bone fastener in conjunction with a pusher mechanism of an applying instrument.

FIG. 1E illustrates the staple in conjunction with a pusher 110 for applying the staple to bone or hard tissue. Pusher 110 has legs 111 which are adapted to apply a driving force directly onto the projecting impact surface 104A of tips 104. Surface 112 engages the crosspiece 103 when impact is applied to keep the tips 104 from being driven apart from the ends of legs 102. As the tips penetrate bone this surface pushes the staple into the channels left by the tips. The driving force may be applied manually by the surgeon, or through the use of a powered instrument.

Figures 2, 3:
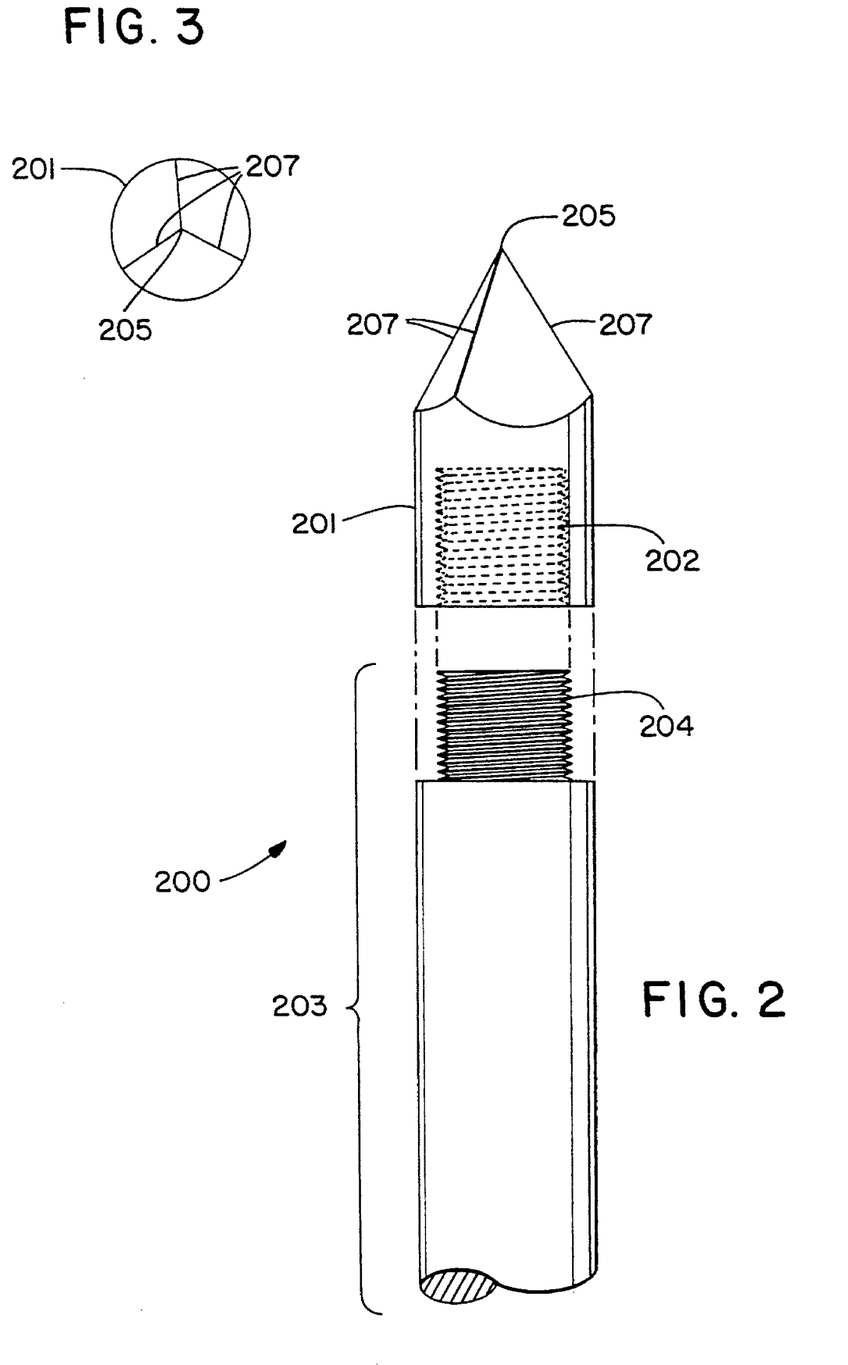
FIG. 2 illustrates an exploded side view of a pin type fastener of the present invention.
FIG. 3 illustrates an end view of the trocar point of the present invention.

FIGS. 2 and 3 illustrate another embodiment of the present invention. In this embodiment, surgical pin fastener 200 comprises a bioabsorbable fastening body portion in the form of a shaft 203, said body or shaft 203 having a bone penetrating element 201 attached thereto. Bone penetrating element 201 is optimally a hard trocar tip which is fixed to the shaft 203, and preferably has a relatively sharp point 205 and one or more relatively sharp edges 207, for cutting bone. The surgical pin fastener is substantially uniform in cross-section.

The trocar tip 201 may be constructed from any material having a hardness and strength sufficient for penetrating bone or hard tissue. Examples of appropriate metals and ceramic materials have been recited herein above.

The trocar tip 201 is preferably fixed to the end of shaft 203 by a screw mounting. Projecting screw portion 204 of shaft 203 is received into tapped aperture 202 in the tip 201. Screw portion 204 is preferably an integral part of shaft 203 made of the same bioabsorbable material. Optionally, the joint can be made permanent by adhesively bonding the threaded joint.

Alternative joining methods can be used both for the pin 200 and staple 100. For example, the tips 104 and 201 may be fashioned with a sleeve, the sleeve being crimped onto the fastener structure. Interlocking grooves in the tips 104 and 201 in conjunction with cooperating grooves in the legs 102 and shaft 203 respectively are also envisioned.

Figure 4:
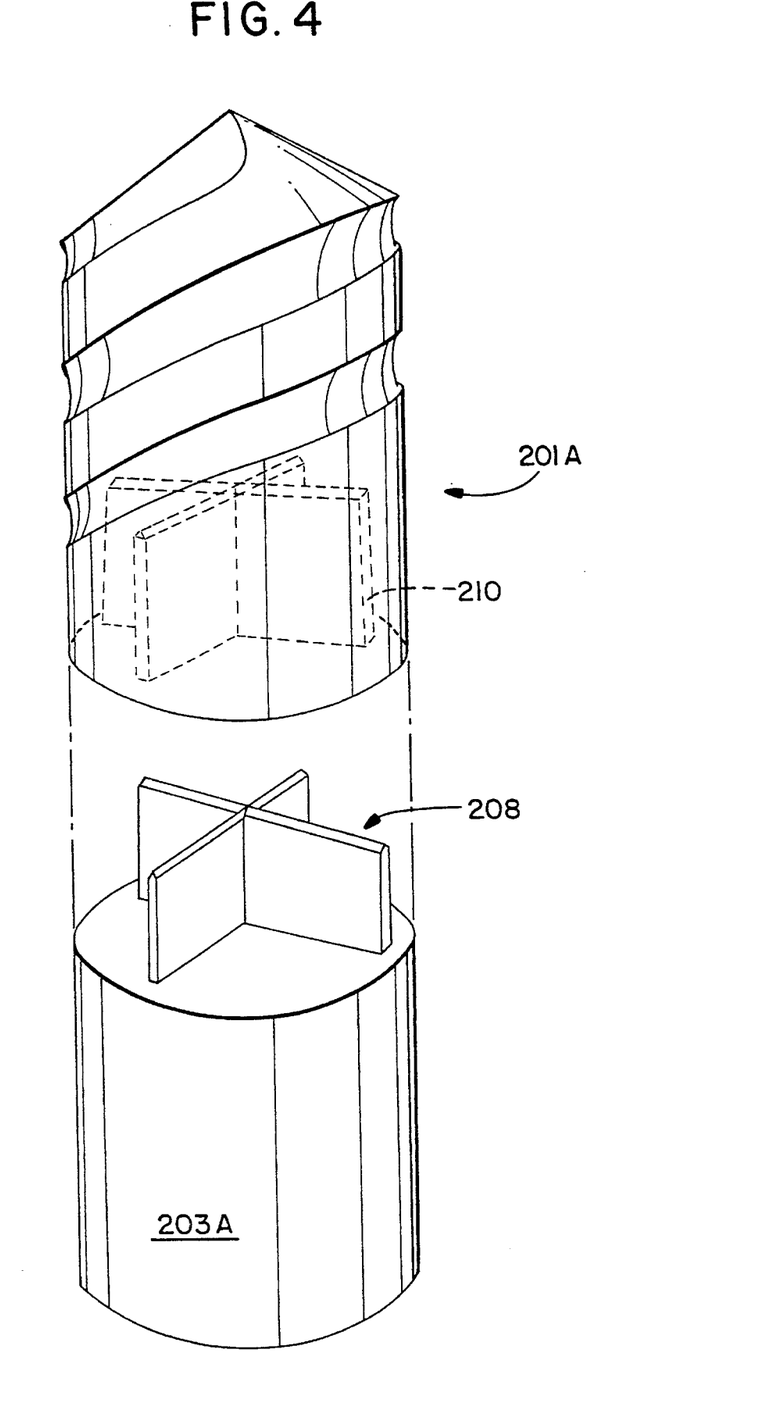
FIG. 4 shows an alternative embodiment of the present invention illustrating alternative tip and mounting fixtures; and, FIG. 5 illustrates another embodiment of the mounting fixture.
Figure 5:
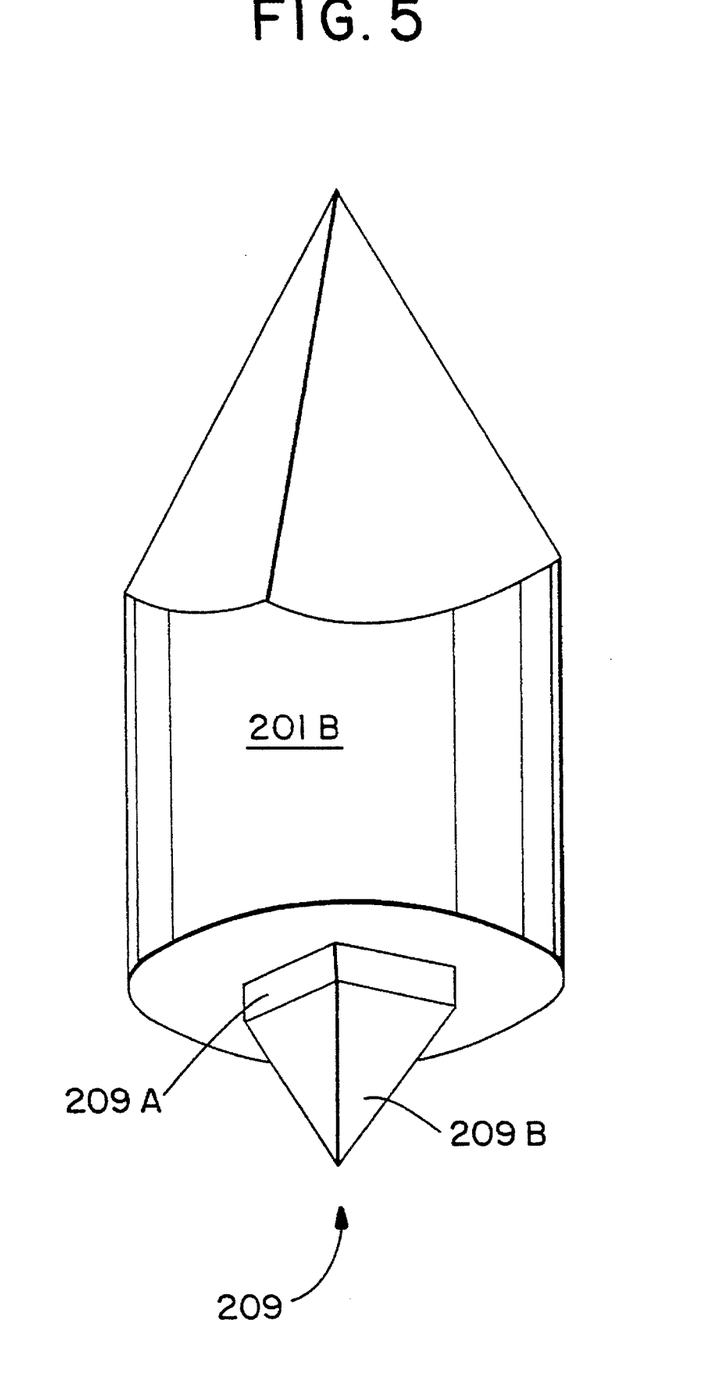

FIG. 4 illustrates alternative embodiments of the tip and shaft. Tip 201A can be fluted in order to function like a drill bit. The shaft 203A may have various types of connection or mounting fixtures, such as the substantially cross shaped male fixture 208 projecting perpendicularly from the end of the shaft, which is adapted to fit into the corresponding female receptacle 210 in the tip 201A. Or, as shown in FIG. 5, trocar tip 201B may have a male mounting fixture 209 adapted to fit into a female receptacle in the shaft. Male mounting fixture 209 optimally has a base portion 209A which projects perpendicularly from the bottom surface of tip 201B, and a pyramid portion 209B which culminates in a point. These tips and shafts may be mounted together adhesively or by welding or fusing the tips and shafts together. Those skilled in the art will envision other types of connection fixtures. It should be realized that the connecting fixtures 208 and 209 can also be used with the staple type bone fastener 100.

Typically, prior art metal bone fastening pins are drilled directly into the bone. Prior art bioabsorbable pins must have predrilled holes into which they are inserted. But in accordance with the present invention, self-inserting pin 200 can be implanted directly into bone by drilling, yet also has the advantage of being bioabsorbable. Alternatively, pin 200 may have a tip 201 with an impact surface, such as the impact surface 104A of the staple fastener 100.

The size of the surgical staple 100 and pin 200 may range from a few millimeters to several centimeters. However, the surgical bone fasteners of the present invention can be made of any size which is appropriate for its function of fastening bone or hard tissue.

Direct implantation of the bioabsorbable fasteners 100 and 200 is possible because the bone penetrating elements (tips 104 and 201) have a bone cutting means, such as relatively sharp points and edges which allow the bone penetrating elements (104 and 201) to pierce the bone when a driving force is applied to the fastener. The driving force can be an impulse or pushing force commonly used for driving staple type fasteners such as fastener 100, or a rotary or drilling force commonly used for pin type fasteners such as 200.

As can readily be seen, the method for using the present invention to fasten segments of bone or hard tissue is relatively simple. Being provided with the surgical fastener of the present invention, the surgeon implants the device into bone or hard tissue so that the bioabsorbable fastening body portion holds and maintains the segments of bone or hard tissue in close adjacency for sufficient period of time to promote healing. Both fasteners 100 and 200 will degrade over a period of time leaving only the metal tips 104 and 201, which, being small, are far less intrusive, and have little tendency to work loose from the bone and migrate.

In some surgical methods employing the fasteners of the present invention no hard nonabsorbable piece at all remains. For example, pin 200 can be driven completely across a fracture site so that the bone penetrating element emerges from the far side of the bone. In such a case, the bone penetrating tip will be cut off and removed, leaving no portion of the fastener which cannot be absorbed.

Figure 6:
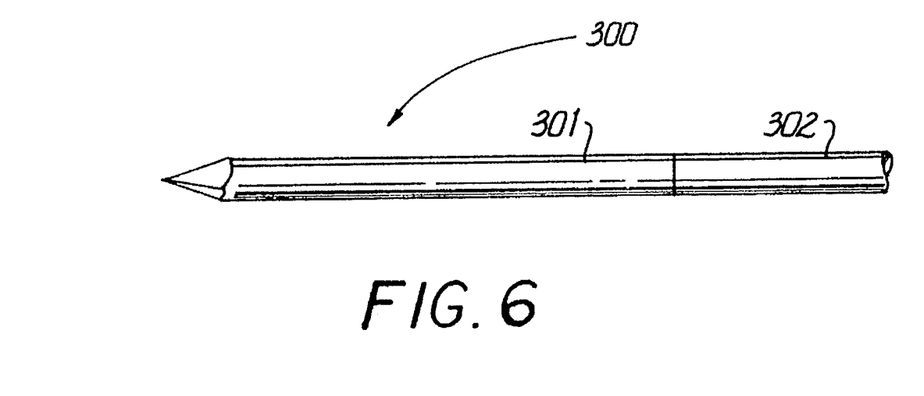
FIG. 6 illustrates an alternative embodiment of the pin fastener of the present invention.

In an alternative embodiment 300 of the present invention illustrated in FIG. 6 the bone piercing element 301 is of sufficient length such that it can be gripped by a drilling device and inserted into bone or hard tissue. The application of a drilling force to the bone penetrating element 301 rather than the absorbable fastener portion or shaft 302 prevents deformation of the relatively softer absorbable fastener portion 302 because it is not subjected to the torsional stress of twisting. The bone penetrating tip 301 is preferably from 3 inches to 8 inches in length. The bioabsorbable shaft portion 302 is preferably from 2 to 4 inches in length. Fastener 300 is substantially uniform in cross-section, i.e. it is not tapered. Uniformity of cross section provides better fitting of the fastener in the bone.

For some surgical applications gripping or drilling may need to be done from both ends of a pin. For example, in operations where a surgeon is required to insert a pin through a first bone fragment and into a second bone fragment across a fracture site, it may happen that the surgeon is satisfied with the positioning of the pin in the second bone fragment but not the first. With a single tipped pin, the surgeon would have to remove the pin altogether, and select a preferred location through the first bone fragment. However, it would be very difficult for the surgeon then to line up the new placement of the pin in the first fragment with the previously made hole in the second fragment.

Figure 7:
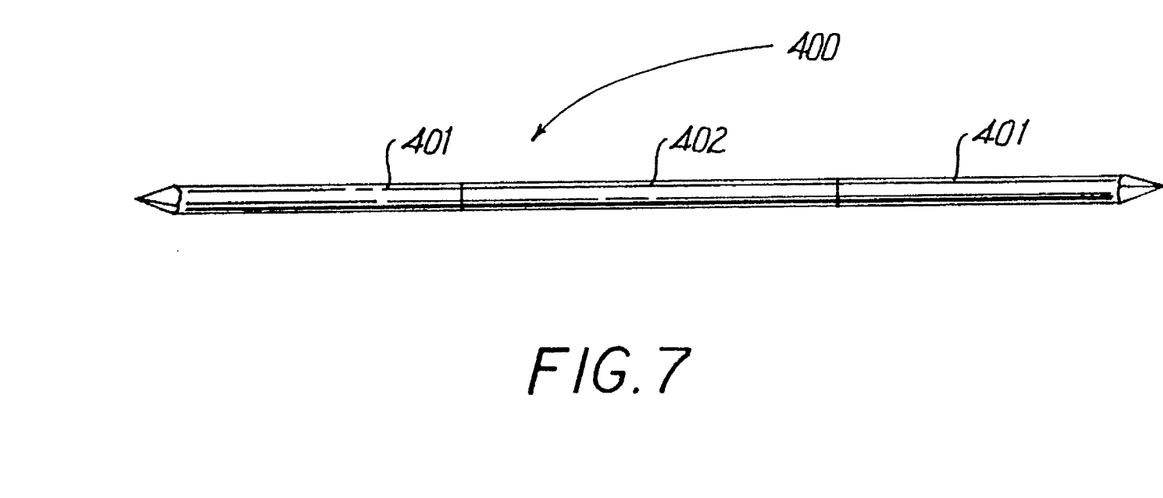
FIG. 7 illustrates a double tipped embodiment of the pin fastener of the present invention.

FIG. 7 illustrates a pin 400 having a bone penetrating element 401 at both ends of a bioabsorbable fastener portion or shaft 402. Pin fastener 400 is preferably substantially uniform in cross section. The bone penetrating element 401 of this embodiment is preferably from 3 to 5 inches in length, and the bioabsorbable center portion 402 is preferably from 2 to 4 inches in length. The tips and shafts can be attached to each other by swaging, crimping, screw fitting, or other methods which one skilled in the art can envision.

With this double tipped pin, the surgeon would pull the pin through the second fragment until the second penetrating element clears the first bone fragment. The surgeon would reapply the pin through the first fragment by means of the second bone penetrating tip.

The tips 301 and 401 are fabricated from material which has hardness and strength suitable for its purpose of drilling bone. Such materials have been mentioned above and include ceramics and implant grade metal elements and alloys. The bioabsorbable shaft portions are fabricated from any suitable bioabsorbable compound such as those mentioned above.

While the above description contains many specifics, these specifics should not be construed as limitations on the scope of the invention, but merely as exemplifications of preferred embodiments thereof. Those skilled in the art will envision many other variations that are within the scope and spirit of the invention as defined by the claims appended hereto.

What is claimed is:

1. A surgical bone pin comprising bioabsorbable shaft having a distally facing end surface, and at least one bone penetrating element for drilling into bone and having a pointed distal end and a proximally facing proximal end surface in contact with the distally facing end surface of the bioabsorbable shaft, said proximally facing proximal end surface and said distally facing end surface having the same outer diameters, said shaft being uniform in cross section throughout its length, and said bone penetrating element being of sufficient length to be gripped by a drilling means and inserted into bone wherein said shaft and said bone penetrating element are non-rotatably joined by a connecting means which comprises a member projecting from one of said contacting distally and proximally facing end surfaces into a corresponding recess in the other of said contacting distally and proximally facing end surfaces, wherein said projecting member has a non-circular cross-section.

2. The surgical fastener of claim 1 wherein said bone penetrating element is from about 3 to 8 inches in length.

3. The surgical fastener of claim 1 wherein said bone penetrating element is fabricated from a ceramic material.

4. The surgical fastener of claim 3 wherein the ceramic material comprises a material selected from the group consisting of zirconia, alumina, and carbon/carbon composites.

5. The surgical fastener of claim 1 wherein said bone penetrating element is fabricated from a metal.

6. The surgical fastener of claim 5 wherein said metal is selected from the group consisting of stainless steel, titanium, titanium alloy, and cobalt-chromium-molybdenum alloy.

7. The surgical fastener of claim 1 wherein said bioabsorbable shaft is fabricated from a bioabsorbable polymer selected from the group consisting of poly(p-dioxanone), polylactide, polyglycolide, polycaprolactone, poly(orthoesters), and trimethylene carbonate polymer, and copolymers and/or mixtures thereof.

8. The surgical bone pin of claim 1 wherein said projecting member of said connecting means and said corresponding recess of said connecting means are cross-shaped.

9. The surgical bone pin of claim 1 wherein said projecting member of said connecting means and said corresponding recess of said connecting means are pyramidal in shape.

10. A surgical bone pin comprising a bioabsorbable shaft having distally and proximally facing end surfaces, a first bone penetrating element for drilling into bone and having a proximally facing proximal end surface in contact with said distally facing end surface of said bioabsorbable shaft, said proximally facing proximal end surface and said distally facing end surface having the same outer diameter, and a second bone penetrating element for drilling into bone and having a distally facing distal end surface in contact with the proximally facing end surface of said bioabsorbable shaft, said distally facing distal end surface and said proximally facing end surface having the same outer diameter, said shaft having a rectilinear longitudinal axis, said bone penetrating elements being aligned with said longitudinal axis and said bone penetrating elements being of sufficient length to be gripped by drilling means and inserted into bone, wherein said shaft and said bone penetrating element are non-rotatably joined by a connecting means which comprises a member projecting from one of said contacting distally and proximally facing end surfaces into a corresponding recess in the other of said contacting distally and proximally facing end surfaces, wherein said projecting member has a non-circular cross-section.

11. The surgical fastener of claim 10 wherein said bone penetrating elements are from about 3 to 5 inches in length.

12. The surgical fastener of claim 10 wherein the bioabsorbable shaft is fabricated from a polymeric material.

13. The surgical fastener of claim 12 wherein said polymeric material is selected from the group consisting of poly (p-dioxanone), polylactide, polyglycolide, polycaprolactone, and poly (orthoesters).

14. The surgical fastener of claim 10 wherein said bone penetrating elements are fabricated from a metallic material.

15. The surgical fastener of claim 14 wherein said metallic material is selected from the group consisting of stainless steel, titanium, titanium alloys, and cobalt-chromium-molybdenum alloy.

16. The surgical fastener of claim 10 wherein said bone penetrating elements are fabricated from a ceramic material.

17. The surgical fastener of claim 16 wherein said ceramic material is selected from the group consisting of zirconia, alumina, and carbon/carbon composites.

18. A surgical bone pin comprising a bioabsorbable shaft having a distally facing end surface, and at least one non-biodegradable bone penetrating element having a pointed distal end and a proximally facing proximal end surface in contact with the distally facing end surface of the bioabsorbable shaft, said proximally facing proximal end surface of the bone penetrating element and distally facing end surface of the shaft having the same outer diameters, said bioabsorbable shaft having a uniform diameter throughout its length, wherein said shaft and said bone penetrating element are non-rotatably joined by a connecting means which comprises a member projecting from one of said contacting distally and proximally facing end surfaces into a corresponding recess in the other of said contacting distally and proximally facing end surfaces, wherein said projecting member has a non-circular cross-section.

19. The surgical fastener of claim 18 wherein said bone penetrating element has a hardness sufficient for penetrating bone.

20. The surgical fastener of claim 19 wherein said bone penetrating element is a tip.

21. The surgical fastener of claim 20 wherein said tip comprises means for cutting bone.

22. The surgical fastener of claim 21 wherein said means for cutting bone is a relatively sharp point.

23. The surgical fastener of claim 21 wherein said means for cutting bone is at least one relatively sharp edge.

24. The surgical fastener of claim 18 wherein the bioabsorbable fastening body portion is fabricated from a polymeric material.

25. The surgical fastener of claim 24 wherein said polymeric material is selected from the group consisting of poly (p-dioxanone), polylactide, polyglycolide, polycaprolactone, and poly (orthoesters).

26. The surgical fastener of claim 18 wherein said bone penetrating element is fabricated from a metallic material.

27. The surgical fastener of claim 26 wherein said metallic material is selected from the group consisting of stainless steel, titanium, titanium alloys, and cobalt chromium-molybdenum alloy.

28. The surgical fastener of claim 18 wherein said bone penetrating element is fabricated from a ceramic material.

29. The surgical fastener of claim 28 wherein said ceramic material is selected from the group consisting of zirconia, alumina, and carbon/carbon composites.

30. The surgical fastener of claim 18 wherein said bone penetrating element is fixed to the end of said shaft.

31. The surgical fastener of claim 18 wherein said projecting member comprises a substantially cross-shaped member projecting perpendicularly from the end of said shaft.

32. The surgical fastener of claim 18 wherein said projecting member comprises a base portion projecting perpendicularly from the end surface of said bone penetrating element, and a substantially pyramidal portion projecting from said base portion.

33. The surgical fastener of claim 18 wherein the bioabsorbable fastening body portion contains a reinforcing material.

34. The surgical fastener of claim 33 wherein the reinforcing material is at least one type of reinforcing fiber.

35. The surgical fastener of claim 33 wherein the reinforcing material is chosen from the group consisting of polymeric resins and ceramics.

36. A surgical fastener comprising;
   a bioabsorbable shaft having a single longitudinal axis, a distally facing end surface, and a uniform diameter throughout its length; and
   at least one non-biodegradable bone penetrating dement aligned with said longitudinal axis of said shaft, said bone penetrating dement having a pointed distal end and a proximaly facing proximal end surface in contact with the distally facing end surface of said shaft, said proximaly facing proximal end surface of said bone penetrating element and said distally facing end surface of said shaft having the same outer diameter, wherein said shaft and said bone penetrating element are non-rotatably joined by a connecting means which comprises a member projecting from one of said contacting distally and proximally facing end surfaces into a corresponding recess in the other of said contacting distally and proximaly facing end surfaces, wherein said projecting member has a non-circular cross-section.

37. A surgical bone pin comprising a bioabsorbable shaft having a distally facing end surface, and at least one bone penetrating element for drilling into bone and having a pointed distal end and a proximally facing proximal end surface in contact with the distally facing end surface of the bioabsorbable shaft, said proximally facing proximal end surface and said distally facing end surface having the same outer diameters, said shaft being uniform in cross section throughout its length, and said bone penetrating element being of sufficient length to be gripped by a drilling means and inserted into bone, wherein said shaft and said bone penetrating element are joined by a permanent bond, and wherein said shaft and said bone penetrating element are non-rotatingly joined by a connecting means which comprises a member projecting from one of said contacting distally and proximally facing end surfaces into a corresponding recess in the other of said contacting distally and proximally facing end surfaces, said projecting member and said recess having a non-circular cross section.

38. The surgical bone pin of claim 37 wherein said permanent bond is achieved by a method selected from the group consisting of adhesive bonding, welding, and fusing.

* * * * *